United States Patent
Schantz

(10) Patent No.: US 9,926,582 B2
(45) Date of Patent: Mar. 27, 2018

(54) METHOD FOR THE PRODUCTION OF POLYPEPTIDES IN THE PERIPLASM OF PROKARYOTIC CELLS

(71) Applicant: Hoffmann-La Roche Inc., Little Falls, NJ (US)

(72) Inventor: Christian Schantz, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/659,232

(22) Filed: Mar. 16, 2015

(65) Prior Publication Data

US 2015/0275260 A1    Oct. 1, 2015

Related U.S. Application Data

(63) Continuation of application No. PCT/EP2013/068993, filed on Sep. 13, 2013.

(30) Foreign Application Priority Data

Sep. 17, 2012    (EP) .................................... 12184738

(51) Int. Cl.
| | | |
|---|---|---|
| C07K 14/21 | (2006.01) | |
| C12P 21/00 | (2006.01) | |
| C07K 1/14 | (2006.01) | |
| C12P 21/02 | (2006.01) | |
| C07K 14/47 | (2006.01) | |

(52) U.S. Cl.
CPC .............. *C12P 21/00* (2013.01); *C07K 1/145* (2013.01); *C07K 14/21* (2013.01); *C07K 14/47* (2013.01); *C12P 21/02* (2013.01)

(58) Field of Classification Search
None
See application file for complete search history.

(56) References Cited

U.S. PATENT DOCUMENTS 7,087,419 B2 *   8/2006   Thompson ............... C12N 9/18
                                                    435/198

FOREIGN PATENT DOCUMENTS

| CN | 1311255 A | 9/2001 |
|---|---|---|
| JP | 07-184680 | 7/1995 |
| RU | 2488635 C1 | 7/2013 |
| WO | 00/49164 A1 | 8/2000 |
| WO | 02/48376 A2 | 6/2002 |
| WO | 03/059386 | 7/2003 |
| WO | 2005/017174 A2 | 2/2005 |
| WO | 2011/095506 A1 | 8/2011 |

OTHER PUBLICATIONS

Ren, G. et al., "Transloation of alpha-Synuclein Expressed in *Escherichia coli*" Journal of Bateriology 189(7):2777-2786 (2007).
Bortoli-German, I. et al., "Informational Suppression to Investigate Structural Functional and Evolutionary Aspects of the Erwinia chrysanthemi Cellulase EGZ" J. Mol. Biol. 246:82-94 (1995).
Martineau, P. et al., "Expression of an Antibody Fragment at High Levels in the Bacterial Cytoplasm" J. Mol. Biol. 280:117-127 (1998).
Written Opinion issued in International Application No. PCT/EP2013/068993, 7 pages.
Nori Kida, Story No. 65: What is research—How an idea is born, [Online] (Published Aug. 20, 2009) http://www.rikasuki.jp/rika_no65/fika_no65.htm.
Vaara, "Agents That Increase the Permeability of the Outer Membrane" Microbiology Reviews 56(3):395-411 1992.
Yang et al., "The Application of a Novel Lytic System to the Recovery of Recombinant Proteins in E.coli" Acta Biochimica et Biophysica Sinica 32(3):211-216 2000.

* cited by examiner

*Primary Examiner* — Celine Qian
(74) *Attorney, Agent, or Firm* — Rebecca J. Wais

(57) ABSTRACT

Herein is reported a method for producing a polypeptide comprising the step of incubating (resuspended) prokaryotic cells in a solution comprising about 10 mM to about 95 mM Tris-HCl and about 2 mM to about 6 mM EDTA at a pH value of about 7 to about 10 for about 15 min to about 6 h at about 25° C.

9 Claims, 2 Drawing Sheets

METHOD FOR THE PRODUCTION OF POLYPEPTIDES IN THE PERIPLASM OF PROKARYOTIC CELLS

CROSS REFERENCE TO RELATED APPLICATIONS

This application is a continuation of International Application No. PCT/EP2013/068993 having an international filing date of Sep. 13, 2013, the entire contents of which are incorporated herein by reference, and which claims benefit under 35 U.S.C. § 119 to European Patent Application No. 12184738.8 filed on Sep. 17, 2012.

Herein is reported a method for producing a polypeptide in prokaryotic cells wherein the recombinantly produced polypeptide is recovered from the periplasm of the prokaryotic cells using an incubation step in a buffered system in the presence of a chelating agent at defined pH and temperature values.

BACKGROUND OF THE INVENTION

When having an appropriate signal sequence, recombinantly produced polypeptides can be secreted into the periplasmic space of *E. coli* cells (Joly, J. C. and Laird, M. W., in The Periplasm ed. Ehrmann, M., ASM Press, Washington D.C., (2007) 345-360). In the chemically oxidizing environment the formation of disulfide bonds and thereby the functionally correct folding of polypeptides is favored. Selective isolation of these polypeptides from the periplasmic space is desired to avoid contamination with host cell proteins (HCPs) from *E. coli*. Thereby, the subsequent purification of the polypeptides is facilitated.

An exemplary isolation method is the osmotic shock as described e.g. by Ren, G. et al., J. of Bacteriology 189 (2007) 2777-2786. Using this method, EDTA dissolved in TRIS buffer (pH 7.2) destabilizes the outer membrane of prokaryotic cells, which enables the penetration of sucrose into the periplasmic space. The inner membrane is not permeable for sucrose. Subsequently, the TRIS-EDTA buffer is removed by centrifugation and the cells are quickly resuspended in ice-cold, distilled water. Thereby water is soaked into the sucrose-filled periplasmic space and the destabilized outer membrane is disintegrated via the increase of the periplasmic volume. Addition of $MgCl_2$ re-stabilizes the outer membrane.

Additional methods can be found in Humphreys, D. P. (in The Periplasm (ed.) Ehrmann, M. pp. 361-388. Washington, D.C.: ASM Press (2007)) and Middelberg, A. P. (Biotechnol. Adv. 13 (1995) 491-551).

According to Joly and Laird (see supra) "common methods for isolating periplasmic fractions at small scale such as spheroplasting or osmotic shock treatment are not practically accomplished once cultures reach volumes at and above 10 liters". The "recovery of the protein from the external medium or after a disruption of only the outer membrane and peptidoglycan is still a goal that has not been put into practice on large scale" (page 354).

In WO 2012/013930 purification of recombinant protein from sample or extract of Gram-negative bacterial host cell expressing recombinant protein and disulfide isomerase DsbC, involves adjusting pH of sample or extract to precipitate and separate DsbC is reported. New antibody specific for human tumor necrosis factor (TNF)-alpha, useful for treating TNF-alpha mediated diseases, e.g. congestive heart failure, septic or endotoxic shock, cachexia and adult respiratory distress syndrome is reported in WO 01/94585. In US 2005/048056 preparing a tumor necrosis factor-alpha antibody having a heavy and light chain comprises fermenting a cell mixture, forming a cell pellet and allowing the pellet to stand for a hold time is reported.

In WO 2007/106120 modulating tissue distribution of a peptide molecule comprises administering to the tissue a conjugate molecule comprising serum albumin binding peptide is reported. Peptide ligands with affinity for immunoglobulin (Ig) G, IgM and/or human serum albumin which may be conjugated and used to prolong the elimination halftime of active agents from the circulation are reported in WO 01/45746. In US 2004/001827 modulating tissue distribution of a peptide molecule, for enhancing therapeutic efficacy and reducing side effects, comprises administering to the tissue a conjugate molecule comprising a peptide ligand domain and an active domain is reported.

SUMMARY OF THE INVENTION

In the current invention it has been found that a recombinantly produced polypeptide can be isolated from the periplasm of a prokaryotic cell by contacting or incubating the cell with a solution comprising a buffering agent (e.g. Tris) and a chelating agent (e.g. EDTA) at a pH value of about 8 and at room temperature. The method enables the isolation of a recombinantly produced polypeptide in high yields and purity in large scale production processes. The isolated polypeptide shows good feasibility for downstream processes (e.g. purification).

One aspect as reported herein is a method for producing a polypeptide comprising the step of incubating prokaryotic cells in a solution comprising about 10 mM to about 95 mM of a buffering agent and about 0.5 mM to about 9.5 mM of a chelating agent at a pH value of about 7 to about 10 for about 15 min to about 6 h.

In one embodiment the chelating agent is selected from the group comprising ethylendiamine, nitrilotriacetic acid (NTA), ethylene glycol tetraacetic acid (EGTA), diethylene triamine pentaacetic acid (DTPA), 1,2-bis(o-aminophenoxy) ethane-N,N,N',N'-tetraacetic acid (BAPTA), Ethylenediamine-N,N'-disuccinic acid (EDDS), phosphonates (e.g. Ethylenediamine tetra(methylene phosphonic acid) EDTMP or Diethylenetriamine penta(methylene phosphonic acid) DTPMP), citrate, porphyrines (e.g. heme, chlorophyll or vitamin B12). In one embodiment the chelating agent is ethylenediaminetetraacetic acid (EDTA).

One aspect as reported herein is method for producing a polypeptide comprising the step of incubating (resuspended) prokaryotic cells in a solution comprising about 10 mM to about 95 mM Tris-HCl and about 2 mM to about 6 mM EDTA at a pH value of about 7 to about 10 for about 15 min to about 6 h at about 25° C.

One aspect as reported herein is method for producing a polypeptide comprising the step of incubating (resuspended) prokaryotic cells in a solution comprising about 10 mM to about 95 mM Tris-HCl and about 2 mM to about 4 mM EDTA at a pH value of about 7 to about 10 for about 15 min to about 6 h at about 25° C.

In one embodiment the concentration of the chelating agent is from about 1 mM to about 6 mM. In one embodiment the concentration of the chelating agent is from about 1 mM to about 4 mM. In one embodiment the concentration of the chelating agent is from about 1 mM to about 3 mM. In one embodiment the concentration of the chelating agent is from about 2 mM to about 6 mM. In one embodiment the concentration of the chelating agent is from about 2 mM to about 4 mM. In one embodiment the concentration of the chelating agent is about 2 mM. In one embodiment the concentration of the chelating agent is about 4 mM. In one embodiment the concentration of the chelating agent is about 6 mM.

In one embodiment the concentration of EDTA is from about 0.5 mM to 9.5 mM. In one embodiment the concentration of EDTA is from about 1 mM to about 3 mM. In one embodiment the concentration of EDTA is about 2 mM. In one embodiment the concentration of EDTA is about 4 mM. In one embodiment the concentration of EDTA is about 6 mM.

In one embodiment the method as reported herein is characterized in that the EDTA concentration is about 2 mM.

In one embodiment the method as reported herein is characterized in that the EDTA concentration is about 4 mM.

In one embodiment the method as reported herein is characterized in that the EDTA concentration is about 6 mM.

In one embodiment the solution has a pH value of about 7.5 to about 8.5. In one embodiment the method as reported herein is characterized in that the pH value is about 8.

In one embodiment the incubation time is about 20 min to about 3.5 hours. In one embodiment the method as reported herein is characterized in that the incubation time is about 30 min.

In one embodiment the buffering agent is a substance interacting with the outer membrane of prokaryotic cells.

In one embodiment the buffering agent is a monovalent organic amine. In one embodiment the buffering agent is tris(hydroxymethyl)aminomethane (Tris) or salts thereof.

In one embodiment the buffering agent is selected from the group comprising phosphoric acid or salts thereof, morpholine or salts thereof (MOPS), 3-{[tris(hydroxymethyl)methyl]amino}propanesulfonic acid (TAPS), N,N-bis(2-hydroxyethyl)glycine (Bicine), N-tris(hydroxymethyl)methylglycine (Tricine), 3-[N-Tris(hydroxymethyl)methylamino]-2-hydroxypropanesulfonic acid (TAPSO), 4-2-hydroxyethyl-1-piperazineethanesulfonic acid (HEPES), 2-{[tris(hydroxymethyl)methyl]amino}ethanesulfonic acid (TES), histidine or salts thereof, glycine or salts thereof, or tris(hydroxymethyl)aminomethane (Tris) or salts thereof. In one embodiment the salt is Tris-HCl.

In one embodiment the concentration of Tris-HCl is from about 10 mM to about 95 mM. In one embodiment the concentration of Tris-HCl is from about 15 mM to about 50 mM. In one embodiment the concentration of Tris-HCl is from about 20 mM to about 60 mM. In one embodiment the method as reported herein is characterized in that the concentration of Tris-HCl is about 20 mM. In one embodiment the method as reported herein is characterized in that the concentration of Tris-HCl is about 40 mM. In one embodiment the method as reported herein is characterized in that the concentration of Tris-HCl is about 60 mM.

In one embodiment the method is performed at room temperature. In one embodiment the method as reported herein is performed at 20° C. to 33° C. In one embodiment the method as reported herein is performed at about 25° C.

In one embodiment the method for producing a polypeptide comprises the step of incubating (resuspended) prokaryotic cells in a solution comprising about 10 mM to about 95 mM Tris-HCl and about 2 mM EDTA at a pH value of about 7 to about 10 for about 15 min to about 6 h at about 25° C.

In one embodiment the method as reported herein is characterized in that the prokaryotic cell is a Gram-negative cell.

In one embodiment the prokaryotic cell is a resuspended cell.

In one embodiment the prokaryotic cell is selected from the group of gram negative bacteria which have an outer membrane. In one embodiment the prokaryotic cell is selected from the genus *Acetobacter, Bacteroides, Borrelia, Bortadella, Burkholderia, Campylobacter, Chlamydia, Citrobacter, Enterobacter, Escherichia, Fusobacterium, Helicobacter, Hemophilus, Klebsiella, Legionella, Leptospiria, Neisseria, Nitrobacter, Proteus, Pseudomonas, Rickettsia, Salmonella, Serratia, Shigella, Thiobacter, Treponema, Vibrio, Xanthomonas* or *Yersinia*. In one embodiment the method as reported herein is characterized in that the prokaryotic cell is an *E. coli* cell.

In one embodiment the polypeptide is a non-glycosylated polypeptide.

In one embodiment the polypeptide is an antibody or an antibody fragment. In one embodiment the antibody fragment is selected from Fv, Fab, Fab', Fab'-SH, F(ab')$_2$; diabodies; linear antibodies; single-chain antibody molecules (e.g. scFv); and multispecific antibodies formed from antibody fragments.

In one embodiment the solution used in the method as reported herein is substantially free of peptidoglycan hydrolyzing enzymes. In one embodiment the peptidoglycan hydrolyzing enzyme is selected from lysozymes (muramidases), lytic transglycosylases, N-acetyl-β-D-glucosaminidases, N-acetylmuramyl-L-alanine amidases or endopeptidases.

In one embodiment the solution used in the method as reported herein is substantially free of sugar. In one embodiment the sugar is sucrose.

In one embodiment the solution used in the method as reported herein is substantially free of sugar and substantially free of peptidoglycan hydrolyzing enzymes. In one embodiment the solution used in the method as reported herein is substantially free of sucrose and substantially free of lysozyme.

In one embodiment the method further comprises after the incubating step the step of isolating the polypeptide.

In one embodiment the method comprises the step of purifying the isolated polypeptide.

In one embodiment the method is characterized in that the EDTA concentration is about 2 mM, the pH value is about 8, the incubation time is about 30 min, the concentration of Tris-HCl is about 20 mM, the incubation temperature is about 25° C. and the prokaryotic cell is an *E. coli* cell.

In one embodiment the method is characterized in that the EDTA concentration is about 4 mM, the pH value is about 8, the incubation time is about 30 min, the concentration of Tris-HCl is about 40 mM, the incubation temperature is about 25° C. and the prokaryotic cell is an *E. coli* cell.

In one embodiment the method is characterized in that the EDTA concentration is about 6 mM, the pH value is about 8, the incubation time is about 30 min, the concentration of Tris-HCl is about 60 mM, the incubation temperature is about 25° C. and the prokaryotic cell is an *E. coli* cell. One aspect as reported herein is the use of a method as reported herein for the isolation of a periplasmic polypeptide from a prokaryotic cell.

DETAILED DESCRIPTION OF THE INVENTION

Definitions

Figure 1:
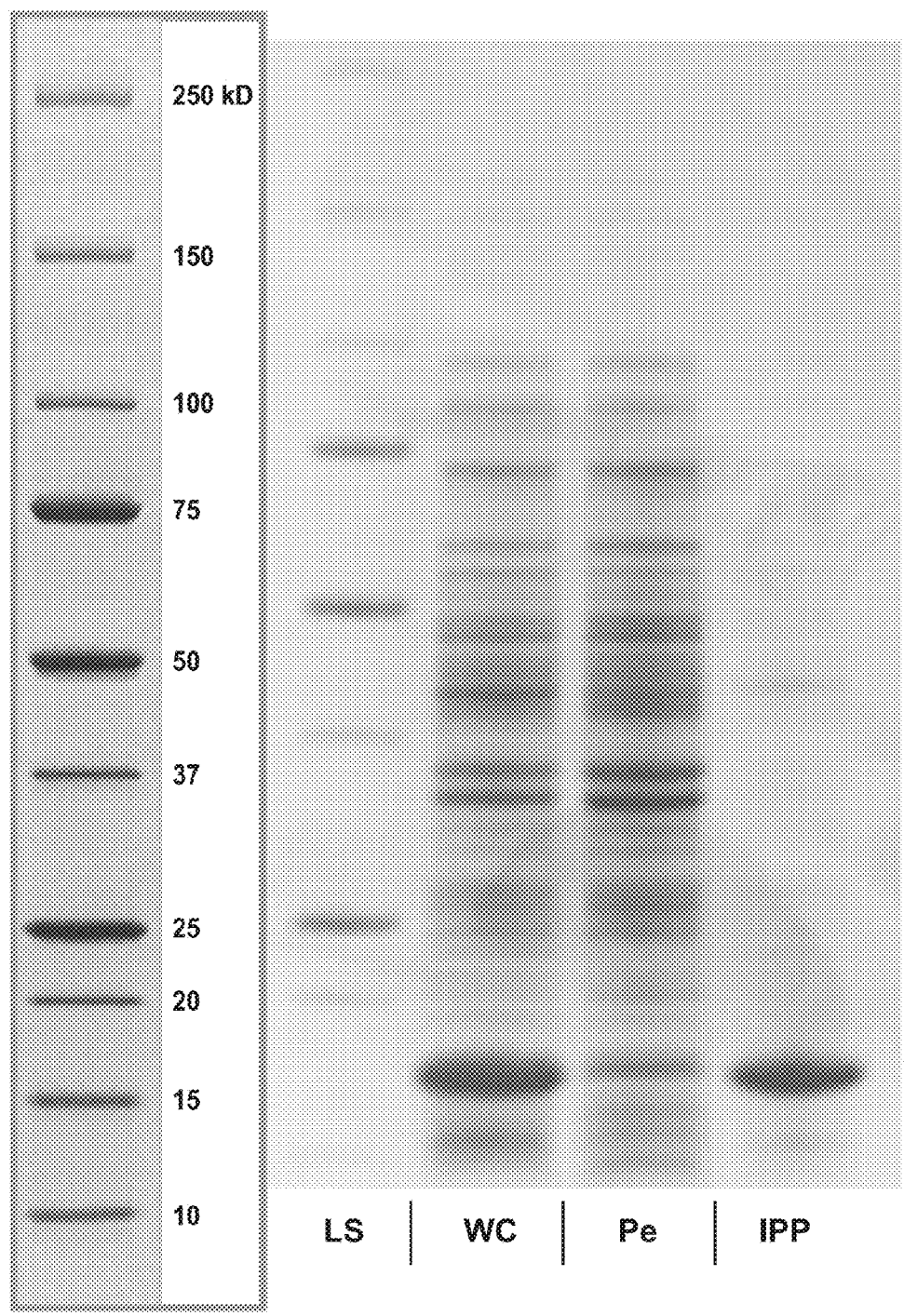
FIG. 1: SDS-Page gel of large scale isolation of periplasmic expressed protein (α-Synculein) with the method as reported herein; lanes: LS =length standard, WC=whole cells, Pe=cell pellet, IPP=isolated periplasmic protein.

The term "periplasmic space" or "periplasm" denotes a space bordered by two selective permeable barriers, e.g.

biological membranes. In one embodiment the periplasm is located between the inner membrane (i.e. cytoplasmic membrane) and the outer membrane in Gram-negative bacteria.

The term "chelating agent" denotes a substance that can form several bonds to a single metal ion. In other words, a chelating agent is a multidentate ligand.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "buffered" as used within this application denotes a solution in which changes of pH due to the addition or release of acidic or basic substances is leveled by a buffering agent. Any buffering agent resulting in such an effect can be used. In one embodiment pharmaceutically acceptable buffering agents are used, such as e.g. phosphoric acid or salts thereof (useful pH range 6.8-8.2), morpholine or salts thereof (MOPS, useful pH range 6.5-7.9), 3-{[tris(hydroxymethyl)methyl]amino}propanesulfonic acid (TAPS, useful pH range 7.7-9.1), N,N-bis(2-hydroxyethyl)glycine (Bicine, useful pH range 7.6-9.0), N-tris(hydroxymethyl)methylglycine (Tricine, useful pH range 7.4-8.8), 3-[N-Tris(hydroxymethyl)methylamino]-2-hydroxypropanesulfonic acid (TAPSO useful pH range 7.0-8.2), 4-2-hydroxyethyl-1-piperazineethanesulfonic acid (HEPES, useful pH range 6.8-8.2), 2-{[tris(hydroxymethyl)methyl]amino}ethanesulfonic acid (TES, useful pH range 6.8-8.2), histidine or salts thereof (5.5-7.5), glycine or salts thereof (8.7-10.7), or tris(hydroxymethyl)aminomethane (Tris, useful pH range 7.5-9.0) or salts thereof. In one embodiment the pharmaceutically acceptable buffering agent is phosphoric acid or salts thereof, or tris(hydroxymethyl)aminomethane (Tris) or salts thereof.

The buffer capacity of a buffering agent is at a maximum p[H+]=pKa. It falls to 33% of the maximum value at p[H+]=pKa±1 and to 10% at p[H+]=pKa±1.5. For this reason the useful range is approximately pKa±1.

The term "recombinant" refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant DNA polymerase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant polypeptide" is a polypeptide made using recombinant techniques, i.e., through the expression of a recombinant nucleic acid as depicted above. It is optionally isolated or purified.

An "isolated polypeptide" is a polypeptide that is essentially free from contaminating cellular components, such as carbohydrate, lipid, or other proteinaceous impurities associated with the polypeptide in nature. Typically, a preparation of an isolated polypeptide contains the polypeptide in a highly purified form, i.e. at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. In some embodiments, an polypeptide is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87. However, the term "isolated" does not exclude the presence of the same polypeptide in alternative physical forms, such as dimers, derivatized forms, not correctly folded forms, not correctly disulfide bridged forms, or scrambled forms.

A "polypeptide" is a polymer of amino acid residues joined by peptide bonds, whether produced naturally or synthetically. Polypeptides of less than about 20 amino acid residues are referred to as "peptides." A "protein" is a molecule comprising one or more polypeptide chains whereof at least one comprises 100 or more amino acid residues. Polypeptides and protein may also comprise non-amino acid components, such as carbohydrate groups. Carbohydrate groups and other non-amino acid components may be added by the cell in which the polypeptide or protein is produced, and will vary with the type of cell. Polypeptides and proteins are defined herein in terms of their amino acid backbone structures; substituents such as carbohydrate groups are generally not specified, but may be present nonetheless.

The Method as Reported Herein

One aspect as reported herein is a method for producing a polypeptide comprising the step of incubating prokaryotic cells in a solution comprising about 10 mM to about 95 mM of a buffering agent and about 0.5 mM to about 9.5 mM of a chelating agent at a pH value of about 7 to about 10 for about 15 min to about 6 h.

For recombinant production of a polypeptide, nucleic acid encoding the polypeptide is isolated and inserted into one or more vectors for further cloning and/or expression in a host cell.

Suitable host cells for cloning or expression of polypeptide-encoding vectors include prokaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B.K.C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In the current invention it has been found that a recombinantly produced polypeptide can be isolated from the periplasm of a prokaryotic cell by contacting or incubating the cell with a solution comprising a buffering agent (e.g. Tris) and a chelating agent (e.g. EDTA) at a pH value of about 8 and at room temperature. The method enables the isolation of a recombinantly produced polypeptide in high yields and purity in large scale production processes. The isolated polypeptide shows good feasibility for downstream processes (e.g. purification).

With the method as reported herein the periplasmic polypeptides are selectively liberated from the cells compared for example to lysis/mechanical disruption of whole cells.

Additionally, the method as reported herein does not require the presence of peptidoglycan hydrolyzing enzymes, such as lysozyme, i.e. the method is performed in the absence of lysozyme or any other peptidoglycan hydrolyzing enzyme, i.e. the solution is substantially free of lysozyme or any other peptidoglycan hydrolyzing enzyme.

Furthermore, the method as reported herein is suitable for the preparation of temperature-sensitive polypeptides.

Moreover, the method as reported herein does not require the presence of sucrose or any other sugar, i.e. the method is performed in the absence of sucrose or any other sugar, i.e. the solution is substantially free of sucrose or any other sugar.

In the following table exemplary yields obtainable under different conditions are depicted.

| experiment | EDTA [mM] | incubation time [h] | incubation temperature [° C.] | pH value | TRIS [mM] | isolated protein of interest [%] |
|---|---|---|---|---|---|---|
| reference (whole cells without incubation) | n.a. | n.a. | n.a. | n.a. | n.a. | 100 |
| conditions as reported herein | 2 | 0.5 | 25 | 8 | 20 | 104 |
| comparative conditions 1 | 2 | 0.5 | 31 | 8 | 100 | 95 |
| comparative conditions 10 | 2 | 0.5 | 49 | 8 | 100 | 85 |
| comparative conditions 18 | 0 | 16 | 25 | 8 | 20 | 94 |
| comparative conditions 21 | 0 | 0.5 | 25 | 8 | 20 | 66 |
| comparative conditions 12 | 18 | 0.5 | 31 | 8 | 100 | 84 |
| comparative conditions 17 | 18 | 0.5 | 49 | 8 | 100 | 48 |

Using an incubation time of 16 hours in the absence of EDTA a good yield of protein can be obtained (comparative condition 18).

It has been found in the current invention that the incubation time can be reduced if a low concentration of EDTA, e.g. below 10 mM, such as 2 mM or 4 mM or 6 mM, is added to the incubation mixture. Under these conditions in the presence of EDTA a comparable yield compared to the incubation in the absence of EDTA can be achieved.

It has been found that an increase in temperature above about 25° C. results in a decrease in the obtainable yield.

It has been found that a pH value below a pH value of about 8 (e.g. pH 6.8) results in a decrease in the obtainable yield. An increased pH value can result in an increased yield.

It has been found that the concentration of the employed Tris buffer has to be below 100 mM, e.g. below 50 mM, such as about 20 mM.

It has been found that these results generated in small scale (150 μL isolation volume) can be transferred to larger scales to isolate periplasmic protein from cells cultivated in fermenters. This will facilitate the production of recombinant proteins for market supply.

For large scale production in some cases in might be advantageous to increase the concentration of buffering and chelating agents in connection with reducing buffer volumes.

In the current invention it has been found that the periplasmic expressed protein of interest can effectively be isolated using the method of the invention (see FIG. 1).

In certain embodiments, a polypeptide is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including production by recombinant host cells (e.g. *E. coli* or phage), as described herein.

General chromatographic methods and their use are known to a person skilled in the art. See for example, Chromatography, 5$^{th}$ edition, Part A: Fundamentals and Techniques, Heftmann, E. (ed), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991), Scopes, Protein Purification: Principles and Practice (1982); Sambrook, J., et al. (ed), Molecular Cloning: A Laboratory Manual, Second Edition, Cold Spring Harbor Laboratory Press, Cold Spring Harbor, N.Y., 1989; Current Protocols in Molecular Biology, Ausubel, F. M., et al. (eds)., John Wiley & Sons, Inc., New York; or Freitag, R., Chromatographical processes in the downstream processing of (recombinant) proteins, Meth. Biotechnol. 24 (2007) 421-453 (Animal cell biotechnology 2$^{nd}$ Edition).

Methods for purifying polypeptides are well established and widespread used. They are employed either alone or in combination. Such methods are, for example, affinity chromatography using thiol ligands with complexed metal ions (e.g. with Ni(II)- and Cu(II)-affinity material) or microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), size exclusion chromatography, and preparative electrophoretic methods (such as gel electrophoresis, capillary electrophoresis) (Vijayalakshmi, M. A., Appl. Biochem. Biotech. 75 (1998) 93-102).

The following examples, figures and sequences are provided to aid the understanding of the present invention, the true scope of which is set forth in the appended claims. It is understood that modifications can be made in the procedures set forth without departing from the spirit of the invention.

EXAMPLES

General Method as Reported Herein
Resuspend harvested cells in 20 mM Tris-HCl buffer (pH 8)
Addition of 20 mM Tris-HCl-4 mM EDTA buffer (pH 8) with a ratio of 1:1
Incubation for 30 min at 25° C. with shaking
Separation of cells from supernatant which contains the proteins of the periplasmic space

Example 1

Determination of the Amount of Recombinantly Produced Protein

The current example has been performed in order to determine the amount of recombinantly produced protein of interest isolatable from the periplasmic space of *E. coli* using different methods.

Reference value:
Whole cell lysate corresponding to 100% of protein of interest obtained by disintegrating cells without any pre-treatment.

Sample amount:
All methods were performed taking the cells comprised in a cultivation sample corresponding to 3 OD values (3/OD=ml). The cells have been obtained by centrifugation.

Sample preparation of whole cells for SDS PAGE analysis:
150 µl of PBS were added to the cells followed by addition of 150 µl of SDS sample preparation buffer. After heating to 95° C. for 10 min with shaking, 5 µl were applied to the SDS gel.

Sample preparation of cells extracts using periplasmic recovering for SDS PAGE analysis:
Pelleted cells were resuspended using 150 µl of ice cold TRIS-buffer with or without EDTA.
The resuspended cells were incubated at defined temperature under shaking After incubation the mixture was centrifuged at 10,000×g for 10 min.
The pellet was discarded.
150 µl of SDS sample preparation buffer were added to the supernatant. After heating to 95° C. for 10 min with shaking, 5 µl were applied to the SDS gel.

Comparative Experimental Parameters and Results (Set 1):

| experiment | EDTA [mM] | incubation time [h] | incubation temperature [° C.] | pH value | TRIS [mM] | isolated protein of interest [%] |
|---|---|---|---|---|---|---|
| reference (whole cells) | n.a. | n.a. | n.a. | n.a. | n.a. | 100 |
| comparative conditions 1 | 2 | 0.5 | 31 | 8 | 100 | 95 |
| comparative conditions 2 | 2 | 1.5 | 31 | 8 | 100 | 92 |
| comparative conditions 3 | 18 | 1.5 | 31 | 8 | 100 | 91 |
| comparative conditions 4 | 10 | 1.5 | 37 | 8 | 100 | 89 |
| comparative conditions 5 | 10 | 1 | 31 | 8 | 100 | 87 |
| comparative conditions 6 | 2 | 1 | 37 | 8 | 100 | 87 |
| comparative conditions 7 | 10 | 1 | 37 | 8 | 100 | 87 |
| comparative conditions 8 | 18 | 1 | 37 | 8 | 100 | 87 |
| comparative conditions 9 | 10 | 0.5 | 37 | 8 | 100 | 85 |
| comparative conditions 10 | 2 | 0.5 | 49 | 8 | 100 | 85 |
| comparative conditions 11 | 2 | 1.5 | 49 | 8 | 100 | 85 |
| comparative conditions 12 | 18 | 0.5 | 31 | 8 | 100 | 84 |
| comparative conditions 13 | 10 | 1 | 37 | 8 | 100 | 84 |
| comparative conditions 14 | 10 | 1 | 37 | 8 | 100 | 84 |
| comparative conditions 15 | 10 | 1 | 49 | 8 | 100 | 84 |
| comparative conditions 16 | 18 | 1.5 | 49 | 8 | 100 | 74 |
| comparative conditions 17 | 18 | 0.5 | 49 | 8 | 100 | 48 |

Comparative Experimental Parameters and Results (Set 2):

| experiment | EDTA [mM] | incubation time [h] | incubation temperature [° C.] | pH value | TRIS [mM] | isolated protein of interest [%] |
|---|---|---|---|---|---|---|
| reference (whole cells) | n.a. | n.a. | n.a. | n.a. | n.a. | 100 |
| comparative conditions 18 | 0 | 16 | 25 | 8 | 20 | 94 |
| comparative conditions 19 | 0 | 16 | 25 | 6.8 | 20 | 72 |
| comparative conditions 20 | 0 | 4 | 25 | 8 | 20 | 68 |
| comparative conditions 21 | 0 | 0.5 | 25 | 8 | 20 | 66 |
| comparative conditions 22 | 0 | 16 | 25 | 8 | 100 | 62 |
| comparative conditions 23 | 0 | 16 | 25 | 6.8 | 100 | 57 |
| comparative conditions 24 | 0 | 4 | 25 | 8 | 100 | 48 |
| comparative conditions 25 | 0 | 4 | 25 | 6.8 | 20 | 42 |
| comparative conditions 26 | 0 | 0.5 | 25 | 8 | 100 | 40 |
| comparative conditions 27 | 0 | 0.5 | 25 | 6.8 | 20 | 35 |
| comparative conditions 28 | 0 | 0.5 | 25 | 6.8 | 100 | 35 |
| comparative conditions 29 | 0 | 4 | 25 | 6.8 | 100 | 34 |
| comparative conditions 30 | 0 | 4 | 25 | 7.4 | 60 | 34 |
| comparative conditions 31 | 0 | 4 | 25 | 7.4 | 60 | 32 |

-continued

| experiment | EDTA [mM] | incubation time [h] | incubation temperature [° C.] | pH value | TRIS [mM] | isolated protein of interest [%] |
|---|---|---|---|---|---|---|
| comparative conditions 32 | 0 | 4 | 25 | 7.4 | 60 | 27 |

Comparative Experimental Parameters and Results (Set 3):

| experiment | EDTA [mM] | incubation time [h] | incubation temperature [° C.] | pH value | TRIS [mM] | isolated protein of interest [%] |
|---|---|---|---|---|---|---|
| reference (whole cells) | n.a. | n.a. | n.a. | n.a. | n.a. | 100 |
| conditions as reported herein | 2 | 0.5 | 25 | 8 | 20 | 104 |
| comparative conditions 33 | 2 | 0.5 | 25 | 8 | 50 | 96 |
| comparative conditions 34 | 2 | 0.5 | 25 | 8 | 100 | 98 |

Example 2

Large-Scale Production of Low Molecular Weight Transport Protein (α-Synuclein)

An *E. coli* cell comprising a nucleic acid encoding a low molecular weight transport protein (α-Synuclein) was cultivated in a 10 L fermenter. At the end of the cultivation 9.52 L with an OD value of 78 measured at 578 nm were harvested. This corresponds to 817 g wet cell weight.

Of these, 110 g pelleted cells were resuspended in 5 L of incubation buffer (20 mM TRIS, 2 mM EDTA, pH 8). After incubation for 30 min at 25° C. with agitation cells were separated from the supernatant, which contains the protein of interest from the periplasmic space, by centrifugation with 4700 rpm for 60 min at 4° C.

The low molecular weight transport protein was selectively isolated from the periplasmic space with a yield of 94.9%.

It has been found that the periplasmic expressed protein of interest can effectively be isolated using the method of the invention (see FIG. 1).

Example 3

Large-Scale Production *Pseudomonas* Exotoxin (Nlys-PE25-LR8M)

An *E. coli* cell comprising a nucleic acid encoding a *Pseudomonas* exotoxin (Nlys-PE25-LR8M) was cultivated and harvested according to Example 2.

106 g pelleted cells were resuspended in 5 L of incubation buffer (20 mM TRIS, 2 mM EDTA, pH 8). After incubation for 30 min at 25° C. with agitation cells were separated from the supernatant, which contains the protein of interest from the periplasmic space, by centrifugation with 4700 rpm for 60 min at 4° C.

The *Pseudomonas* exotoxin was selectively isolated from the periplasmic space.

Figure 2:
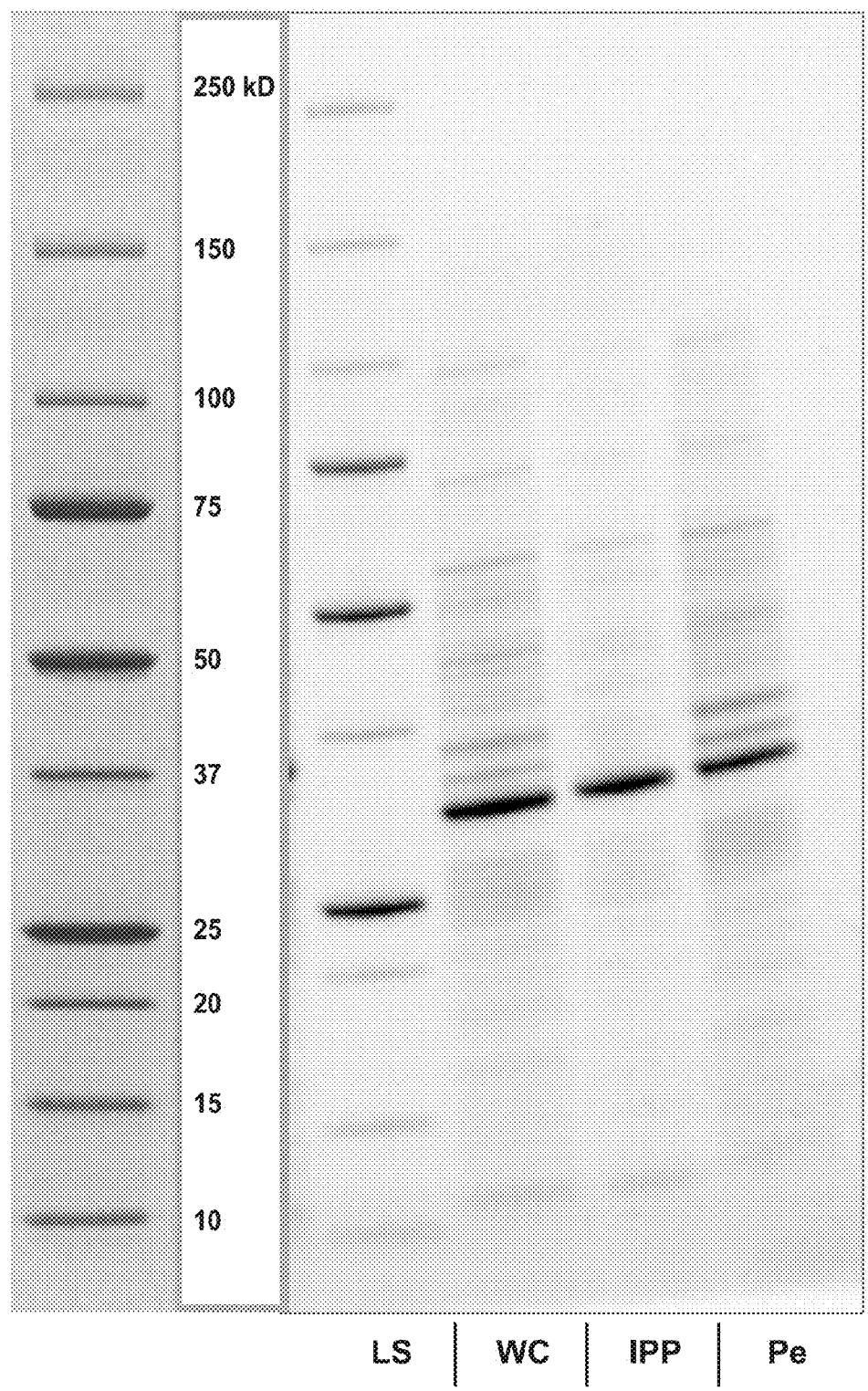
FIG. 2: SDS-Page gel of large scale isolation *Pseudomonas* exotoxin (Nlys-PE25-LR8M) with the method as reported herein; lanes: LS=length standard, WC=whole cells, IPP=isolated periplasmic protein, Pe=cell pellet.

It has been found that the protein of interest can effectively be isolated from the periplasmic space using the method of the invention (see FIG. 2).

The invention claimed is:

1. A method for isolating a recombinant polypeptide from prokaryotic cells comprising: incubating prokaryotic cells in a solution comprising 10 mM to 95 mM Tris and 2 mM to 6 mM EDTA at a pH value of 7 to 10 for 15 min to 6 h at 20° C. to 33° C., wherein the solution is substantially free of sugar and peptidoglycan hydrolyzing enzymes; and isolating the recombinant polypeptide from the solution.

2. The method of claim 1, wherein the pH value is 8.

3. The method of claim 1, wherein the prokaryotic cells are incubated for 30 min.

4. The method of claim 1, wherein the concentration of Tris is 20 mM.

5. The method of claim 1, wherein the prokaryotic cell is a gram-negative cell.

6. The method of claim 5, wherein the prokaryotic cell is an *E. coli* cell.

7. The method of any one of claims 1 to 6, wherein the polypeptide is isolated from periplasm of said prokaryotic cells.

8. The method of claim 7, wherein the periplasmic polypeptide is selected from the group consisting of: an antibody, a non-glycosylated polypeptide, a temperature sensitive polypeptide, alpha-synuclein (α-Synuclein) and Pseudomonas exotoxin (Nly-PE25-LR8M).

9. The method of claim 1, wherein said prokaryotic cells are resuspended in the incubating step.

* * * * *